(12) United States Patent
Matier et al.

(10) Patent No.: US 8,383,648 B2
(45) Date of Patent: *Feb. 26, 2013

(54) AMELIORATION OF THE DEVELOPMENT OF CATARACTS AND OTHER OPHTHALMIC DISEASES

(75) Inventors: William L. Matier, Hockessin, DE (US); Ghanshyam Patil, Lincoln University, PA (US)

(73) Assignee: Colby Pharmaceutical Company, San Jose, CA (US)

( * ) Notice: Subject to any disclaimer, the term of this patent is extended or adjusted under 35 U.S.C. 154(b) by 1063 days.

This patent is subject to a terminal disclaimer.

(21) Appl. No.: 12/141,166

(22) Filed: Jun. 18, 2008

(65) Prior Publication Data
US 2008/0274983 A1 Nov. 6, 2008

Related U.S. Application Data

(62) Division of application No. 10/440,583, filed on May 19, 2003, now Pat. No. 7,442,711.

(51) Int. Cl.
*A01N 43/40* (2006.01)
*A61K 31/445* (2006.01)
(52) U.S. Cl. ........... 514/315; 514/18; 514/317; 514/327
(58) Field of Classification Search .................. 514/18, 514/315, 317, 327
See application file for complete search history.

(56) References Cited

U.S. PATENT DOCUMENTS

| | | | |
|---|---|---|---|
| 3,936,456 A | 2/1976 | Ramey et al. |
| 4,014,335 A | 3/1977 | Arnold |
| 4,287,175 A | 9/1981 | Katz |
| 4,343,787 A | 8/1982 | Katz |
| 4,404,302 A | 9/1983 | Gupta et al. |
| 4,615,697 A | 10/1986 | Robinson |
| 4,691,015 A | 9/1987 | Behrens et al. |
| 4,804,539 A | 2/1989 | Guo et al. |
| 4,818,537 A | 4/1989 | Guo |
| 4,851,436 A | 7/1989 | Hoffman et al. |
| 4,871,742 A | 10/1989 | Bonne et al. |
| 4,883,658 A | 11/1989 | Holly |
| 4,914,088 A | 4/1990 | Glonek et al. |
| 4,927,891 A | 5/1990 | Kamath et al. |
| 4,983,392 A | 1/1991 | Robinson |
| 5,004,770 A | 4/1991 | Cortolano et al. |
| 5,075,104 A | 12/1991 | Gressel et al. |
| 5,145,893 A | 9/1992 | Galbo et al. |
| 5,188,928 A | 2/1993 | Karino et al. |
| 5,209,927 A | 5/1993 | Gressel et al. |
| 5,225,196 A | 7/1993 | Robinson |
| 5,278,151 A | 1/1994 | Korb et al. |
| 5,290,888 A | 3/1994 | Gatechair et al. |
| 5,294,607 A | 3/1994 | Glonek et al. |
| 5,399,473 A | 3/1995 | Shono et al. |
| 5,462,946 A | 10/1995 | Mitchell et al. |
| 5,466,233 A | 11/1995 | Weiner et al. |
| 5,475,013 A | 12/1995 | Talley et al. |
| 5,518,732 A | 5/1996 | Nigam |
| 5,578,586 A | 11/1996 | Glonek et al. |
| 5,707,643 A | 1/1998 | Ogura et al. |
| 5,718,922 A | 2/1998 | Herrero-Vanrell et al. |
| 5,869,079 A | 2/1999 | Wong et al. |
| 5,902,598 A | 5/1999 | Chen et al. |
| 5,981,548 A | 11/1999 | Paolini et al. |
| 5,981,584 A | 11/1999 | Egbertson et al. |
| 6,001,853 A | 12/1999 | Zigler et al. |
| 6,149,925 A | 11/2000 | Mammone et al. |
| 6,154,671 A | 11/2000 | Parel et al. |
| 6,251,090 B1 | 6/2001 | Avery et al. |
| 6,281,192 B1 | 8/2001 | Leahy et al. |

(Continued)

FOREIGN PATENT DOCUMENTS

| | | |
|---|---|---|
| CA | 2029402 | 5/1991 |
| CA | 2065796 | 10/1992 |

(Continued)

OTHER PUBLICATIONS

El-Remessy, et al., "Neuroprotective effect of (−)Delta9-tetrahydrocannabinol and cannabidiol in N-methyl-D-aspartate-induced retinal neurotoxicity: Involvement of peroxynitrite", American Journal of Pathology, Nov. 1, 2003, vol. 163(5), pp. 1997-2008.

(Continued)

*Primary Examiner* — Yong Chong
(74) *Attorney, Agent, or Firm* — Woodcock Washburn LLP

(57) ABSTRACT

Ophthalmically acceptable compositions used in arresting the development of cataracts or macular degeneration comprising a pharmaceutically acceptable carrier or diluent and a compound having the formula:

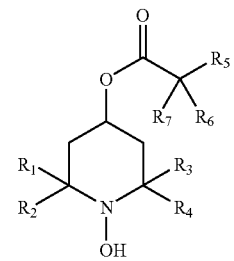

where $R_1$ and $R_2$ are, independently, H or $C_1$ to $C_3$ alkyl;
$R_3$ and $R_4$ are, independently $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is or $C_1$ to $C_6$ alkyl, alkenyl, alkynyl, or substituted alkyl or alkenyl;
$R_7$ is $C_1$ to $C_6$ alkyl, alkenyl, alkynyl, or substituted alkyl or alkenyl
or where $R_6$ and $R_7$, or $R_5$, $R_6$ and $R_7$, taken together, form a carbocycle or heterocycle having from 3 to 7 atoms in the ring.

17 Claims, 1 Drawing Sheet

U.S. PATENT DOCUMENTS

| | | |
|---|---|---|
| 6,331,313 B1 | 12/2001 | Wong et al. |
| 6,375,972 B1 | 4/2002 | Guo et al. |
| 6,410,045 B1 | 6/2002 | Schultz et al. |
| 6,429,194 B1 | 8/2002 | Leahy et al. |
| 6,433,007 B1 | 8/2002 | Garner et al. |
| 7,442,711 B2 | 10/2008 | Matier et al. |
| 7,825,134 B2 | 11/2010 | Matier et al. |
| 2003/0109566 A1 | 6/2003 | Mano et al. |
| 2004/0002461 A1 | 1/2004 | Matier et al. |

FOREIGN PATENT DOCUMENTS

| | | |
|---|---|---|
| DE | 38 01 790 A1 | 7/1989 |
| DE | 40 00 551 A1 | 7/1990 |
| DE | 42 00 192 A1 | 7/1992 |
| DE | 43 27 297 A1 | 2/1994 |
| DE | 44 11 369 A1 | 10/1994 |
| DE | 43 20 444 A1 | 12/1994 |
| DE | 44 24 706 A1 | 1/1995 |
| DE | 44 26 222 A1 | 3/1995 |
| DE | 196 16 185 A1 | 10/1996 |
| DE | 196 18 197 A1 | 11/1997 |
| DE | 198 16 681 A1 | 10/1998 |
| DE | 197 35 255 A1 | 2/1999 |
| EP | 0 138 767 B2 | 3/1988 |
| EP | 0 157 738 B1 | 4/1989 |
| EP | 0 378 054 A3 | 7/1990 |
| EP | 0 490 771 A1 | 6/1992 |
| EP | 0 356 677 B1 | 6/1993 |
| EP | 0 309 400 B1 | 3/1994 |
| EP | 0 352 221 B1 | 3/1994 |
| EP | 0 309 401 B2 | 10/1994 |
| EP | 0 627 428 A1 | 12/1994 |
| EP | 0 638 616 A1 | 2/1995 |
| EP | 0 467 850 B1 | 7/1995 |
| EP | 0 467 848 B1 | 1/1996 |
| EP | 195 30 468 A1 | 2/1997 |
| EP | 0 565 487 B1 | 4/1997 |
| EP | 0 588 763 B1 | 12/1997 |
| EP | 0 508 398 B1 | 7/1998 |
| EP | 0 601 745 B1 | 3/1999 |
| EP | 0 665 294 B1 | 5/1999 |
| EP | 0 644 195 B1 | 7/1999 |
| EP | 0 761 466 B1 | 8/1999 |
| EP | 0 775 684 B1 | 8/1999 |
| EP | 0 641 822 B1 | 12/1999 |
| EP | 0 745 646 B1 | 7/2001 |
| EP | 0 636 610 B1 | 3/2002 |
| EP | 0 943 665 B1 | 11/2003 |
| EP | 0 934 972 B1 | 4/2004 |
| GB | 2 253 411 A | 9/1992 |
| JP | 58-99449 | 6/1983 |
| JP | 63-85547 | 4/1988 |
| JP | 3-31342 | 2/1991 |
| JP | 4288302 | 10/1992 |
| JP | 9-52975 | 2/1997 |
| JP | 10-45777 | 2/1998 |
| JP | 10-45778 | 2/1998 |
| JP | 10-219140 | 8/1998 |
| JP | 10-220381 | 8/1998 |
| JP | 2000-327844 | 11/2000 |
| WO | WO 95/17900 A1 | 7/1995 |
| WO | WO 96/37576 | 11/1996 |
| WO | WO 97/26879 A | 7/1997 |
| WO | WO 97/39051 | 10/1997 |
| WO | WO 97/39052 | 10/1997 |
| WO | WO 98/27149 | 6/1998 |
| WO | WO 98/28256 A1 | 7/1998 |
| WO | WO 98/47893 A1 | 10/1998 |
| WO | WO 98/50360 A1 | 11/1998 |
| WO | WO 99/05108 A1 | 2/1999 |
| WO | WO 99/33911 A1 | 7/1999 |
| WO | WO 99/43666 A2 | 9/1999 |
| WO | WO 00/25740 A1 | 11/2000 |
| WO | WO 01/17738 A1 | 3/2001 |
| WO | WO 01/76576 A2 | 10/2001 |
| WO | WO 02/34262 A1 | 5/2002 |
| WO | WO 03/096991 | 11/2003 |
| WO | WO 03/103622 | 12/2003 |

OTHER PUBLICATIONS

Wang, et al., "Tempol, a superoxide dismutase mimic, ameliorates light-induced retinal degeneration", Research communications in Molecular Pathology and Pharmacology, Sep. 1995, vol. 89(3), pp. 291-305.

Zigler, et al., "Tempol-H inhibits opacification of lenses in organ culture", Free radical Biology & Medicine, Nov. 15, 2003, vol. 35(10), pp. 1194-1202.

Barbarin, F., et al., "L'effet gem effect: measurement of interfunctional distance by electron paramagnetic resonance," Nouv. J. Chim., 1980, 4(7), 437-444 (English Abstract).

Carlsson, D.J., et al., "Photostabilization of polypropylene by a hindered amine," J. of Polym. Science: Polym. Letts. Ed., 1981, 19, 549-554.

Carlsson, D.J., et al., "Hindered amines as antioxidants in UV exposed polymers," Polym. Science Technol. (Plenum), 1984, 26(Polym. Addit.), 35-47.

Chen, K., et al., "Oxidation of hydroxylamines to nitroxide spin labels in living cells," Biochim. et Biophys. Acta, 1988, 970, 270-277.

Chmela, Š., et al., "The influence of substituents on the photo-stabililizing efficiency of hindered amine stabilizers in polypropylene," Polym. Degrad. & Stab., 1990, 27, 159-167.

Ciba-Geigy, A.-G., "NOR (Nitrogen-oxygen-R) hindered amine light stabilizers in polymeric microparticles," Res. Discl., 1991, 323, 155-157 (English abstract).

Dragutan, I., et al., "New amino-nitroxide spin labels," Bioorg. & Med. Chem., 1996, 4(10), 1577-1583.

Klemchuk, P.P., et al., "Stabilization mechanisms of hindered amines," Polym. Degrad. Stab., 1988, 22, 241-274.

Kokhanov, Y., et al., "Synthesis of some heterocyclic radicals of the iminoxyl class," Khim. Geterotsikl. Soedin., 1971, 11, 1527-1529.

Kurosaki, T., et al., "Polymers having stable radicals. II. Synthesis of nitroxyl polymers from 4-methacryloyl derivatives of 1-hydroxy-2,2,6,6-tetramethylpiperidine," J. of Polym. Sci.: Polym. Chem. Ed., 1974, 12, 1407-1420.

Litvin, E.F., et al., "Investigation of the stepwise mechanism of the hydrogenation of iminoyxl bi- and polyradicals of platinum and nickel catalysts," Zh. Org. Kim., 1970, 6(12), 2365-2369.

Nethsinghe, L., et al., "Mechanisms of antioxidant action: complementary chain-breaking mechanisms in the mechanostabilization of rubbers," Rubber Chem. & Technol., 1984, 57, 918-925.

Ohkatsu, Y., et al., "Inhibition of antoxidation by hindered amine light stabilizers and their derivatives," Sekiyu Gakkaishi, 1994, 37(4), 395-399.

Zahradnickova, A., et al., "Comparison of the stabilization ability of N-substituted hindered-amine light stabilizers in hydrocarbon model compounds and in polymers," Plasty Kauc., 1987, 24(6), 174-177 (English abstract).

Age-Releated Eye Disease Study Research Group, AREDS Report No. 8, Arch. Ophthalmol., 2001, 119, 1417-1436.

Ahmed, I., et al., "Physicochemical determinants of drug diffusion across the conjunctiva, sclera, and cornea," J. of Pharm. Sci., 1987, 76(8), 583-586.

Ambati, J., et al., "Age-related macular degeneration: etiology, pathogenesis, and therapeutic strategies," Survey of Ophthalmology, 2003, 48(3), 257-293.

Augustin, A.J., et al, "Oxidative reactions in the tear fluid of patients suffering from dry eyes," Graefe's Arch. Clin. Exp. Ophthalmol., 1995, 233, 694-698.

Berra, A., et al., "Age-related antioxidant capacity of the vitreous and its possible relationship with simultaneous changes in photoreceptors, retinal pigment epithelium and Brushs' membrane in human donors' eyes," Arch. Gerontol. Geriatrics, 2002, 34, 371-377.

Čejková, J., et al., "reactive oxygen species (ROS)-generating oxidases in the normal rabbit cornea and their involvement in the corneal damage evoked by UVB rays," Histol and Histopathol, 2001, 16, 523-533.

Foster, C.S., et al., "Efficacy of etanercept in preventing relapse of uveitis controlled by methotrexate," Arch. Ophthalmol., 2003, 121, 437-440.

Harris, M.D., et al., "Laser eye injuries in military occupations," Aviat. Space Environ. Med., 2003, 74(9), 947-952.

Hartwick, A.T.E., "Beyond intraocular pressure: neuroprotective strategies for future glaucoma therapy," Optometry and Vision Science, 2001, 78(2), 85-94.

Hayashi, S., et al., "Oxygen free radical damage in the cornea after excimer laser therapy," Br. J. Ophthalmol., 1997, 81, 141-144.

Hosseini, K., et al., "Non-invasive monitoring of commonly used intraocular drugs against endophthalmitis by raman spectroscopy," Lasers in Surg. Med., 2003, 32, 265-270.

Izzotti, A., et al., "Oxidative deoxyribonucleic damage in the eyes of glaucoma patients," Am. J. Med., 2003, 114, 638-646.

Kasetsuwan, N., et al., "Effect of topical ascorbic acid on free radical tissue damage and inflammatory cell influx in the cornea after excimer laser corneal surgery," Arch. Ophthalmol., 1999, 117, 649-652.

Lou, M.F., "Redox regulation in the lens," Prog. Retinal & Eye Res., 2002, 22, 657-682.

McDonald, H.F., et al., "Operating microscope-induced retinal phototoxicity during pars plana vitrectomy," Arch. Ophthalmol., 1988, 106, 521-523.

Moffat, B.A., et al., "Age-related changes in the kinetics of water transport in normal human lenses," Exp. Eye Res., 1999, 69, 663-669.

Moritera, T., et al., "Microspheres of biodegradable polymers as a drug-delivery system in the vitreous," Invest. Ophthalmol. Vis. Sci., 1991, 32(6), 1785-1790.

Osborne, N.N., et al., "Some current ideas on the pathogenesis and the role of neuroprotection in glaucomatous optic neuropathy," Eur. J. Ophthalmol., 2003, 13(Suppl. 3), S19-S26.

Pavilack, M.A., et al., "Site of potential operating microscope light-induced phototoxicity on the human retina during temporal approach eye surgery," Ophthalmol., 2001, 108(2), 381-385.

Stone, D.U., et al., "Ocular rosacea: an update on pathogenesis and therapy," Curr. Opin. Ophthalmol., 2004, 15(6), 499-502.

Wein, F.B., et al., "Current understanding of neuroprotection in glaucoma," Curr. Op. Ophthalmol., 2002, 13, 61-67.

Zamir, E., et al., "Nitroxide stable radical suppresses autoimmune uveitis in rats," Free Rad. Biol. Med., 1999, 27, 7-15.

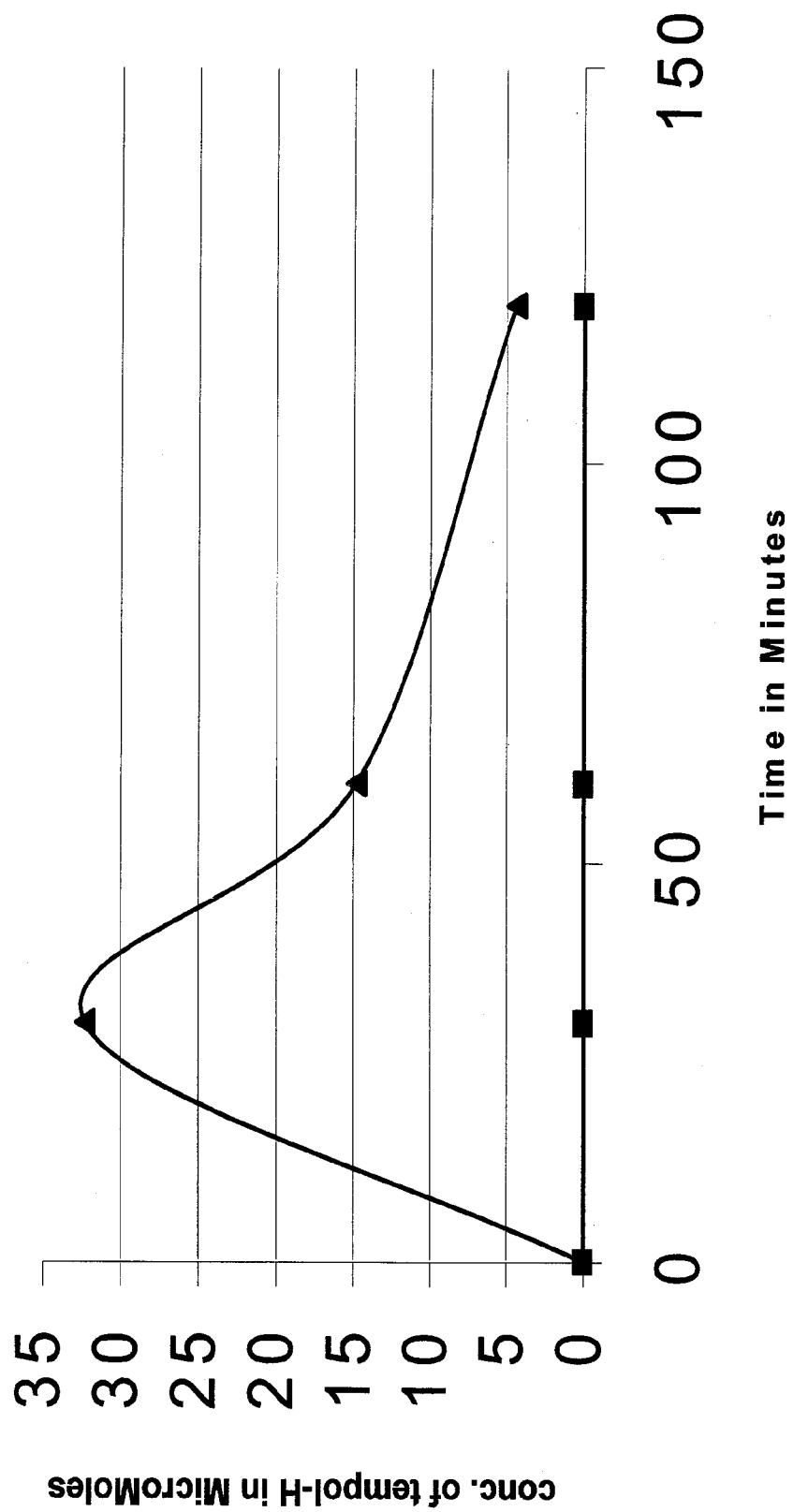
Bioavailability after dosing with compound 1 and tempol-H

AMELIORATION OF THE DEVELOPMENT OF CATARACTS AND OTHER OPHTHALMIC DISEASES

CROSS REFERENCE TO RELATED APPLICATIONS

This application is a divisional of U.S. application Ser. No. 10/440,583, filed May 19, 2003, which claims the benefit of U.S. Provisional Application No. 60/381,287, filed May 17, 2002, the entireties of which are incorporated herein.

FIELD OF THE INVENTION

The present invention is directed to compositions that ameliorate the development of cataracts in the eye of a patient and to methods for effecting such amelioration. In preferred embodiments of the invention, cataract development or growth is essentially halted. The present invention is also directed to the treatment of macular degeneration in the eye and to certain other uses. In accordance with preferred embodiments, the compositions of this invention are capable of administration to patients without the need for injections and can be formulated into eye drops for such administration. Methods for treatment of cataracts and macular degeneration are also provided, as are methods for the preparation of the novel compounds and compositions useful in the practice of the invention.

BACKGROUND OF THE INVENTION

Aging-related cataract results from gradual opacification of the crystalline lens of the eye. This disease is presently treated by surgical removal and replacement of the affected lens. It is believed that once begun, cataract development proceeds via one or more common pathways that culminate in damage to lens fibers. This condition progresses slowly and occurs predominantly in the elderly. Alternatively, cataract may form because of surgical, radiation or drug treatment of a patient, e.g. after surgery of an eye to repair retinal damage (vitrectomy) or to reduce elevated intraocular pressure; x-irradiation of a tumor; or steroid drug treatment. A significant retardation of the rate of cataract development in such patients may eliminate the need for many surgical cataract extractions. This reduction would provide tremendous benefits both to individual patients and to the public health system.

It has been known to provide certain hydroxylamine compositions for the prevention or retardation of cataracts in the eyes of persons. U.S. Pat. No. 6,001,853, in the name of Zigler, et al., the content of which is incorporated herein by reference, reflects work performed at the National Institutes of Health of the United States. Zigler et al. identified a class of hydroxylamines which, when administered to the eye of a test animal, ameliorates cataract genesis or development. Such administration was necessarily via injection for physico-chemical reasons. While Zigler stated in Example 6, it would be clinically convenient to deliver TEMPOL-H by liquid eye drops, no working example was reported, Zigler's hydroxylamines being actually administered by subconjunctival injections. Zigler's materials were also accompanied by the co-administration of a reducing agent, either via injection, systemically or otherwise. It is believed that subsequent work at the National Institutes of Health was directed to the identification of effective hydroxylamines that could be administered topically, however those efforts were not successful.

Accordingly, it has been the object of intense research activity to identify compounds and compositions containing them that can ameliorate cataract formation and development in the eyes of patients without the need for unpleasant, inconvenient and potentially dangerous intraocular injections. In particular, a long-felt need has existed, which has not been fulfilled, for such compounds and compositions which can be administered via topical application, especially via eye drops. This need is addressed by the present invention.

Age-related macular degeneration is a leading cause of blindness in the United States and many European countries. The "dry" form of the disease is most common. It occurs when the central retina has become distorted, pigmented, or most commonly, thinned. The neovascular "wet" form of the disease is responsible for most severe loss of vision. The wet form of macular degeneration is usually associated with aging, but other diseases which can cause wet macular degeneration include high myopia (being very nearsighted), some intraocular infections like histoplasmosis, and AIDS. Accordingly there is a need for compositions for treatment of such ailments being easily deliverable to the eye of patients in great need.

SUMMARY OF THE INVENTION

The present invention provides compositions for the treatment of cataracts in the eyes of patients either who are developing cataracts or who are known or suspected of being at risk for formation of cataracts. Compositions are also provided for the treatment of macular degeneration in the eyes of patients who may exhibit or will likely exhibit macular degeneration due to disease. In accordance with preferred embodiments, such compositions are formulated in topical liquid form, especially as eye drops. Periodic application of the compositions of this invention retards or halts development of cataracts or macular degeneration in treated eyes. The invention provides compositions, which need not be applied via injection or other uncomfortable or inconvenient routes.

In accordance with preferred embodiments, the present invention provides compositions comprising an ophthalmologically acceptable carrier or diluent and a compound having the formula:

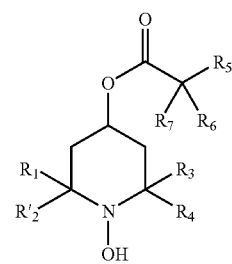

In such compounds, $R_1$ and $R_2$ are, independently, H or $C_1$ to $C_3$ alkyl and $R_3$ and $R_4$ are, independently $C_1$ to $C_3$ alkyl. It is also possible, in accordance with certain embodiments, that $R_1$ and $R_2$, taken together, or $R_3$ and $R_4$, taken together, or both form a cycloalkyl moiety. In the compounds of the invention, $R_5$ is H, OH, or $C_1$ to $C_6$ alkyl while $R_6$ is $C_1$ to $C_6$ alkyl, alkenyl, alkynyl, or substituted alkyl or alkenyl. $R_7$ is $C_1$ to $C_6$ alkyl, alkenyl, alkynyl, or substituted alkyl or alkenyl or $C_1$-$C_6$ cycloalkyl or heterocyclic. It is also possible for $R_6$ and $R_7$, or $R_5$, $R_6$ and $R_7$, taken together, to form a carbocycle or heterocycle having from 3 to 7 atoms in the ring. The term "ophthalmic," as used herein, means to have usefulness in the treatment of the eye and its diseases.

In the compounds used in the compositions of the invention, the substituted alkyl or alkenyl species can be substituted with at least one hydroxy, alkoxy, alkylthio, alkylamino, dialkylamino, aryloxy, arylamino, benzyloxy, benzylamino or heterocyclic or YCO—Z where Y is O, N, or S and Z is alkyl, cycloalkyl or heterocyclic or aryl substituent. In accordance with some embodiments, the heterocycle is a 5, 6, or 7 membered ring with at least one oxygen, sulfur, or nitrogen atom in the ring. In one preferred composition, $R_6$ and $R_7$, taken together are cyclopropyl, while in others, $R_6$ and $R_7$, taken together are tetrahydrofuranyl and $R_5$, $R_6$ and $R_7$ taken together are furanyl.

For certain preferred compounds, each of $R_1$ through $R_4$ is $C_1$ to $C_3$ alkyl, most especially ethyl or methyl, most especially, methyl. For some preferred embodiments, the compounds of the invention $R_6$ is $C_1$ to $C_6$ alkyl substituted with at least one $C_1$ to $C_6$ alkoxy or benzyloxy group.

In other preferred compounds, each of $R_1$ through $R_4$ is methyl, $R_5$ is H or methyl, $R_6$ is methyl substituted with benzyloxy or $C_1$ to $C_6$ alkoxy and $R_7$ is methyl or where $R_6$ and $R_7$ form a cyclopropyl group. In others, each of $R_1$ through $R_4$ is methyl, $R_5$ is methyl, $R_6$ is ethoxy methyl and $R_7$ is methyl. In still others, each of $R_1$ through $R_4$ is methyl, $R_5$ is methyl, $R_6$ is benzyloxy methyl and $R_7$ is methyl, while compounds where each of $R_1$ through $R_4$ is methyl, $R_5$ is methyl, $R_6$ is hydroxymethyl and $R_7$ is methyl also find utility.

Also preferred for some embodiments, are compounds wherein each of $R_1$ through $R_4$ is methyl and $R_5$, $R_6$, and $R_7$ form a furanyl group or where $R_5$ is H and $R_6$ and $R_7$ form a tetrahydrofuranyl group. A further embodiment provides compounds where $R_1$ through $R_4$ are all methyl, $R_5$ is H, and $R_6$ and $R_7$ form a cyclopropyl ring.

It is preferred that the compositions of the invention be formulated into an aqueous medium, which may be delivered in topical liquid form to the eye, via eye drops for example. Accordingly, pH and other characteristics of compositions of the invention are ophthalmologically acceptable for topical application to the eye of a patient. For some embodiments, the compound is in the form of a salt, preferably a hydrochloride or similar salt.

Since the compounds of the invention contain oxidizable hydroxylamine moieties, which are most effective in the chemically reduced state, the compositions preferably further comprise an anti-oxidant agent, especially a sulfhydryl compound. Exemplary compounds include mercaptopropionyl glycine, N-acetylcysteine, β-mercaptoethylamine, glutathione and similar species, although other anti-oxidant agents suitable for ocular administration, e.g. ascorbic acid and its salts or sulfite or sodium metabisulfite may also be employed. The amount of hydroxylamines may range from about 0.1% weight by volume to about 10.0%; weight by volume and preferred is about 0.25%-weight by volume to about 5.0% weight by volume.

The invention can also be seen to provide ophthalmologic compositions comprising an ophthalmologically acceptable carrier or diluent together with a compound having an N-hydroxypiperidine portion bound to a solubility modifying portion. In this way, the active moiety, hydroxylamine, can be delivered to the lens of an eye in need of treatment in a "stealth" form, that is, in the form of a chemical compound that can have the hydroxylamine portion cleaved from the balance of the molecule. The compound is broken down in the eye to give rise to the active hydroxylamine species for effective treatment of cataracts or macular degeneration. The compound thus provided has a solubility in water at 25° C. of at least about 0.1% by weight and a water—n-octanol partition coefficient at 25° C. of at least about 3. In accordance with preferred embodiments, the water solubility is greater than about 0.5% by weight, preferably greater than about 2.0% and the partition coefficient is greater than about 5, preferably greater than about 10.

Accordingly, it is desired that the compounds used be such that, upon administration topically to the eye, they penetrate the cornea and are converted to the desired hydroxylamine, preferably, an N-hydroxypiperidine. It is preferred that this conversion occurs through enzymatic cleavage of the compound. In one preferred embodiment, the hydroxylamine portion comprises—1,4-dihydroxy-2,2,6,6-tetramethylpiperidine.

The invention also provides methods for identifying pharmaceuticals that can be delivered to the lens of a patient in the form of eye drops. These methods comprise selecting a compound having a water solubility at 25° C. of at least about 0.1% by weight and a water/n-octanol partition coefficient of at least about 5 at 25° C., which compound is enzymatically cleavable under conditions obtaining in the eye of a patient to give rise to a proximate drug for treatment of a condition of the eye, preferably the lens. Preferably, the active pharmaceutical species is a hydroxylamine, especially one having an N-hydroxypiperidine nucleus.

The pharmaceutical compositions of the present invention may also be used for treatment of parts of the eye other than the lens. Thus, they are suitable for ameliorating or arresting the development of macular degeneration.

The invention includes methods for ameliorating—either slowing or arresting entirely—the development of a cataract in the lens of a patient. Some of these methods may be used to treat macular degeneration in the eye of a patient. Such methods comprise administering to the eye an ophthalmologic composition comprising an ophthalmologically acceptable carrier or diluent in the form of eye drops containing a compound having one or more of the foregoing compounds as an active ingredient therein. It is preferred that the administration takes place a plurality of time and, in certain preferred embodiments, chronic, periodic administration is performed.

BRIEF DESCRIPTION OF THE DRAWINGS

FIG. 1 depicts aqueous humor levels of Tempol-H (1,4-dihydroxy-2,2,6,6-tetramethylpiperidine) in rabbit eyes treated topically with Compound 1 of the invention or with Tempol-H.

DETAILED DESCRIPTION OF ILLUSTRATIVE EMBODIMENTS

The present invention provides compounds and compositions that can be administered topically to the eyes of patients who are developing or who are at risk of developing cataracts or macular degeneration. While such compounds may be seen to include as a chemical fragment, hydroxylamine species previously known to be effective in retarding cataract development, the achievement of compounds that can be topically applied is a very significant advance in the therapeutic arts. Indeed, the National Institutes of Health, assignee of the Zigler patent; tried, but failed to identify compounds that could be efficacious in therapies for cataracts or macular degeneration through topical application. In this context, it is noted that the Zigler patent recites administration of certain compositions such as TEMPOL-H via injection and recognizes the desirability of topical administration via eye drops, however, this proposed route of administration was not found to be available in practice. Accordingly, the present invention should be viewed as "pioneering" and as having satisfied a long—felt, but unserved need in the art.

The present invention also provides compounds and compositions that can be administered topically to the eyes or lens of a patient who has developed macular degeneration or who is at risk of developing macular degeneration. There is no standard treatment for the "dry" form of macular degeneration although low vision rehabilitation may be available to some extreme cases. The "wet" form maybe treated by laser surgery coupled with low vision rehabilitation. Use of the present invention in treating macular degeneration has not been found to be available in current practice.

While not desiring to be bound by theory, it is believed that the compounds of the present invention are absorbed across the cornea into the eye where enzymatic processes cleave the N-hydroxypiperidine portion of the compound from the acid to which it was esterified. The N-hydroxypiperidine moiety, once liberated, then performs the same functions with the same efficacy as demonstrated by Zigler.

The esters of the invention have not been known heretofore for administration to the eye. They have certainly not been known for use in the treatment of cataract. U.S. Pat. No. 5,981,548, in the name of Paolini, et al., the content of which is incorporated herein by reference, depicts certain N-hydroxylpiperidine esters and their use as antioxidants in a number of contexts. However, Paolini does not disclose ophthalmologic formulations or topical treatment of the eyes of patients. Paolini does disclose, however, useful syntheses for certain molecules of this type.

Gupta et al. in U.S. Pat. No. 4,404,302, the content of which, disclose the use of certain N-hydroxylamines as light stabilizers in plastics formulations. Mitchell et al. in U.S. Pat. No. 5,462,946, the content of which is incorporated herein by reference, discloses certain nitroxides deriving from substituted oxazolidines for protection of organisms from oxidative stress. U.S. Pat. No. 3,936,456, the content of which is incorporated herein by reference, in the name of Ramey et al., provides substituted piperazine dione oxyls and hydroxides for the stabilization of polymers. U.S. Pat. No. 4,691,015, to Behrens et al., the content of which is incorporated herein by reference, describes hydroxylamines derived from hindered amines and the use of certain of them for the stabilization of polyolefins.

The tissues, including the lens, of the anterior chamber of the eye are bathed by the aqueous humor. This fluid is in a highly reducing redox state because it contains antioxidant compounds and enzymes. The lens is also a highly reducing environment, which maintains the hydroxlamine compounds in the preferred reduced form. It may be necessary to include a reducing agent in the eye drop formulation but one skilled in the art may not find it necessary in the present invention to dose separately with the reducing agent or to introduce it into the eye.

Preferred reducing agents may be N-acetylcysteine, ascorbic acid or a salt form, and sodium sulfite or metabisulfite. A combination of N-acetylcysteine and sodium ascorbate may be used. A metal chelator antioxidant, such as EDTA (ethylenediaminetetraacetic acid) or possibly DTPA (diethylenetriaminepentaacetic acid) may also be added to keep the hydroxylamine in the reduced form in the eye drop formulation.

In accordance with one embodiment of the invention, the composition may be delivered to the lens of an eye in need of treatment via polymeric inserts, such as OCUSERT® or a contact lens or other object temporarily resident upon the surface of the eye. Thus, the composition may be incorporated into a contact lens or some other similar means. The composition may also be placed upon the eye in the ordinary fashion, e.g. in eye drops or washes. Alternatively, the compositions may be applied in other ophthalmologic dosage forms known to those skilled in the art, such as preformed or in situ formed gels or liposomes. Application of the anticataract compounds to the eye in these forms also results in enzymatic degradation of the esters into the proximate hydroxylamine therapeutic.

The present invention provides compositions comprising a pharmaceutically carrier or diluent and a compound having the formula:

where $R_1$ and $R_2$ are, independently, H or $C_1$ to $C_3$ alkyl;

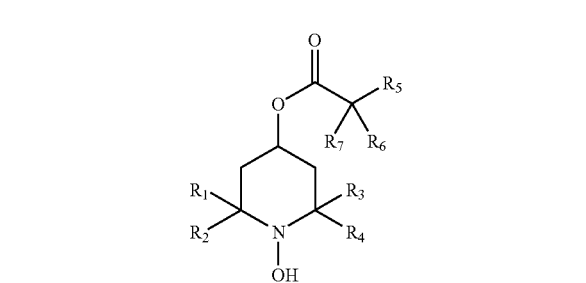

$R_3$ and $R_4$ are, independently $C_1$ to $C_3$ alkyl; and where $R_1$ and $R_2$, taken together, or $R_3$ and $R_4$, taken together, or both may be cycloalkyl;

$R_5$ is H, OH, or $C_1$ to $C_6$ alkyl;

$R_6$ is $C_1$ to $C_6$ alkyl, alkenyl, alkynyl, or substituted alkyl or alkenyl;

$R_7$ is $C_1$ to $C_6$ alkyl, alkenyl, alkynyl, substituted alkyl, alkenyl, cycloalkyl, or heterocycle or where $R_6$ and $R_7$, or $R_5$, $R_6$ and $R_7$, taken together, form a carbocycle or heterocycle having from 3 to 7 atoms in the ring. These compounds may also be used with ophthalmically acceptable carriers for use in ophthalmic compositions.

The compounds of the present invention may also comprise an ophthalmically acceptable carrier or diluent and a compound having an N-hydroxy piperidine portion bound to a solubility modifying portion, the compound having a solubility in water at 25° C. of at least about 0.25% by weight and a water—n-octonal partition coefficient at 25° C. of at least about 5. The composition may have the N-hydroxy piperidine portion cleavable from the compound under conditions found in the eye. It is foreseeable that this portion is cleaved under conditions in the lens of the eye. The N-hydroxy piperidine portion may be cleaved enzymatically. The compositions may also exist wherein the N-hydroxy piperidine portion is 1-oxyl-4-hydroxy-2,2,6,6-tetramethylpiperidyl.

The term $C_1$ to $C_n$ alkyl, alkenyl, or alkynyl, in the sense of this invention, means a hydrocarbyl group having from 1 to n carbon atoms in it. The term thus comprehends methyl, ethyl, n-propyl, iso-propyl, n-butyl, sec-butyl, iso-butyl, tert-butyl, and the various isomeric forms of pentyl, hexyl, and the like. Likewise, the term includes ethenyl, ethynyl, propenyl, propynyl, and similar branched and unbranched unsaturated hydrocarbon groups of up to n carbon atoms. As the context may admit, such groups may be functionalized such as with one or more hydroxy, alkoxy, alkylthio, alkylamino, dialkylamino, aryloxy, arylamino, benzyloxy, benzylamino, heterocycle, or YCO—Z, where Y is O, N, or S and Z is alkyl, cycloalkyl, heterocycle, or aryl substituent.

The term carbocycle defines cyclic structures or rings, wherein all atoms forming the ring are carbon. Exemplary of these are cyclopropyl, cyclobutyl, cyclopentyl, cyclohexyl, cycloheptyl, etc. Cyclopropyl is one preferred species. Heterocycle defines a cyclic structure where at least one atom of the ring is not carbon. Examples of this broad class include furan, dihydrofuran, tetrahydrofuran, pyran, oxazole, oxazoline, oxazolidine, imidazole and others, especially those with an oxygen atom in the ring. Five, six and seven membered rings with at least one oxygen or nitrogen atom in the ring are preferred heterocycles. Furanyl and tetrahydrofuranyl species are among those preferred.

It is preferred for certain embodiments that each of $R_1$ through $R_4$ be lower alkyl that is $C_1$ to $C_3$ alkyl. Preferably, all these groups are methyl for convenience in synthesis and due to the known efficacy of moieties having such substitution at these positions. However, other substituents may be used as well.

In certain embodiments, compounds are employed where $R_6$ is $C_1$ to $C_6$ alkyl substituted with at least one $C_1$ to $C_6$ alkoxy or benzyloxy group. Preferred among these are compounds having ethoxy or benzyloxy substituents. Among preferred compounds are those where each of $R_1$ through $R_4$ is methyl, $R_5$ is H or methyl, $R_6$ is methyl substituted with benzyloxy or $C_1$ to $C_6$ alkoxy, and $R_7$ is methyl or where $R_6$ and $R_7$ form a cyclopropyl group as well as the compound in which each of $R_1$ through $R_4$ is methyl, $R_5$ is methyl, $R_6$ is ethoxy or benzyloxy methyl, and $R_7$ is methyl. An additional preferred compound is one in which each of $R_1$ through $R_4$ is methyl, $R_5$ is methyl, $R_6$ is hydroxymethyl, and $R_7$ is methyl.

Other useful compounds are those wherein each of $R_1$ through $R_4$ is methyl, and $R_5$, $R_6$, and $R_7$ form a furanyl group, or in which $R_6$ and $R_7$ form a tetrahydrofuranyl group. The compound where $R_1$ through $R_4$ is methyl, $R_5$ is H and, $R_6$ and $R_7$ form a cyclopropyl ring is a further preferred species are as those set forth in the examples below.

The compounds of the invention are formulated into compositions for application to the eye of patients in need of therapy. Thus, such compositions are adapted for pharmaceutical use as an eye drop or in contact lenses, inserts or the like. Accordingly, formulation of compound into sterile water containing any desired diluents, salts, pH modifying materials and the like as are known to persons skilled in the pharmaceutical formulations art may be performed in order to achieve a solution compatible with administration to the eye. It may be that eye drops, inserts, contact lenses, gels and other topical liquid forms may require somewhat different formulations. All such formulations consistent with direct administration to the eye are comprehended hereby.

The compositions of the invention may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities.

Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-Acetylcysteine may be present in a range of about 0.1% to about 5.0% weight by volume, with about 1% to about 10% of hydroxylamine concentration being preferred. Ascorbic acid or salt may also be present in a range of about 0.1% to about 5.0% weight by volume with about 1% to about 10% weight by volume of hydroxylamine concentration preferred. Other sulfhydryls, if included, may be the same range as for N-acetylcysteine. Other exemplary compounds include mercaptopropionyl glycine, N-acetyl cysteine, β-mercaptoethylamine, glutathione and similar species, although other anti-oxidant agents suitable for ocular administration, e.g. ascorbic acid and its salts or sulfite or sodium metabisulfite may also be employed.

A buffering agent may be used to maintain the pH of eye drop formulations in the range of about 4.0 to about 8.0; this is necessary to prevent corneal irritation. Because the compounds of this invention are esters, the pH will need to be about 3.5 to about 6.0, preferably about 4.0 to about 5.5, in order to prevent hydrolysis of the ester bond and to ensure at least a 2-year shelf life, for the product. This pH also ensures that most of the hydroxylamine is in its protonated form for highest aqueous solubility. The buffer may be any weak acid and its conjugate base with a pKa of about 4.0 to about 5.5; e.g. acetic acid/sodium acetate; citric acid/sodium citrate. The pKa of the hydroxylamines is about 6.0.

The compounds of the present invention may also include tonicity agents suitable for administration to the eye. Among those suitable is sodium chloride to make formulations of the present invention approximately isotonic with 0.9% saline solution.

In certain embodiments, the compounds of the invention are formulated with viscosity enhancing agents. Exemplary agents are hydroxyethylcellulose, hydroxypropylcellulose, methylcellulose, and polyvinylpyrrolidone. The viscosity agents may exists in the compounds up to about 1.6% weight by volume. It may be preferred that the agents are present in a range from about 0.2% to about 0.25 weight by volume. A preferred range for polyvinylpyrrolidone may be from about 0.1% to about 0.2% weight by volume. One skilled in the art may prefer any range established as acceptable by the Food and Drug Administration.

The compounds of the invention may have cosolvents added if needed. Suitable cosolvents may include glycerin, polyethylene glycol (PEG), polysorbate, propylene glycol, and polyvinyl alcohol. The presence of the cosolvents may exist in a range of about 0.2% to about 1.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, and from about 0.01% to about 0.2% weight by volume of methyl or propylparabens.

For effective treatment of cataract, one skilled in the art may recommend a dosage schedule and dosage amount adequate for the subject being treated. It may be preferred that dosing occur one to four times daily for as long as needed. The dosage amount may be one or two drops per dose. The dosage schedule may also vary depending on the active drug concentration, which may depend on the hydroxylamine used and on the needs of the patient. It may be preferred that the active amount be from about 0.1% to about 10.0% weight by volume. In some embodiments, it is preferable that the active drug concentration be 0.25% to about 5.0% weight by volume.

An ophthalmologist or one similarly skilled in the art may have a variety of means to monitor the effectiveness of the dosage scheme and adjust dosages accordingly. Effectiveness may be determined by the ophthalmologist by observing the degree of opacity of the lens at intervals by slit-lamp examination, or other means and increasing the frequency and/or concentration of the eye drop prescribed, if needed.

Some embodiments of the invention are methods of administering an antioxidant to a mammal comprising contacting the mammal with a composition comprising a pharmaceutically acceptable carrier or diluent and a compound having an N-hydroxy piperidine portion bound to a solubility modifying portion, the compound having a solubility in water at 25° C. of at least about 0.25% by weight and a water—n-octonal partition coefficient at 25° C. of at least about 5. In other embodiments, the methods may identify a pharmaceutical for delivery to the eye of a patient in the form of eye drops comprising selecting a compound having a water solubility at 25° C. of at least about 0.25% by weight and a water—n-octonal partition coefficient of at least about 5 at 25° C., which compound is enzymatically cleavable under conditions obtained in the lens of the eye of a patient to give rise to an N-hydroxy piperidine.

The present invention has optimal use in ameliorating the development of a cataract in the eye of a patient. Another optimal use includes the treatment of macular degeneration in the retina of a patient. The ophthalmic compositions of the present invention may be utilized by administration to the eye of a patient affected by these maladies. This administration may be performed by eye drops, in eye washes, or via other acceptable delivery means known to those skilled in the art such as, dispersion or delivery by contact lens. Other forms of administration of the compositions of the present invention, wherein the delivery to the eye is not called for, may include oral tablets, liquids and sprays; intravenous, subcutaneous and intraperitoneal injections; application to the skin as a patch or ointment; enemas, suppositories, or aerosols.

A variety of esterases is known to be present in ocular tissues, especially the cornea. The specific esterase(s) that cleaves the esters of the present series is not identified. The cleavage of the esters occurs rapidly and essentially completely on administering the compounds to the eyes of rabbits. This is shown by the presence of tempol-H in the aqueous humor at all times (30, 60, 90 and 120 minutes) examined after topical dosing. In contrast, the esters are stable in aqueous solutions; e.g. solution of Ester 4 at 40° C., in acetate buffer at pH 4.6, is stable for 3 months.

It may be preferred that at least 0.1% solubility is needed for an eye drop, even for a suspension formulation. Completely water-insoluble compounds may not be effective. Esters that are soluble in water (>0.1% weight by volume) are preferred. Esters with less than 0.1% solubility may be used in the form of suspensions or ointments or other formulations. Solubility is determined by mixing 100 mg of test compound with 1 ml of water, at room temperature and adding additional 1 ml quantities of water, with mixing, until ester dissolves completely.

Corneal penetration is shown by measuring a substantial concentration (e.g. >5 µM) of the effective hydroxylamine and/or ester in the aqueous humor after administering a solution of the compound in vivo to the eyes of rabbits. This is determined by electron spin resonance (ESR), high performance liquid chromatography (HPLC) or gas chromatography (GC) assay of the rabbit aqueous humor. In vitro corneal penetration methods may also be used prior to the in vivo testing method particularly for screening compounds.

Esters are selected for these tests based on their calculated or measured octanol/water partition coefficient (P). Hydrophilic compounds such as tempol-H cannot penetrate the lipophilic epithelial layer of the cornea. Partition coefficients of tempol-H and esters that penetrate are as follows:

| | P (Calculated)* |
|---|---|
| Tempol-H | 0.8 (measured, 0.5) |
| Ester 4 | 16.4 |
| Ester 8 | 8.2 |
| Ester 14 | 6.3 |

*Clog P version 4.0, Biobyte Corporation

Enzymatic conversion is essentially complete at greater than 90% hydrolysis of the ester in vivo to the alcohol and acid after administering the compound to the eye of rabbits. The conversion may be determined by HPLC or GC assay of the rabbit aqueous humor.

Alternatively, the enzymatic conversion may be determined by incubating the compound in plasma or corneal homogenate and assaying samples periodically by HPLC or GC to monitor the rate of breakdown. Esters with a half-life of less than about 1 or 2 hours are candidates. This method may be the preferred screening procedure before in vivo testing.

Esters should have less than about 10% hydrolysis at 40° C., after 3 months, in aqueous solution at pH 4.0-5.0. This extrapolates to a shelf life of the ester in solution of at least 18 months at room temperature, which may be preferred for an eye drop product.

The compounds of this invention may have uses in fields broader than ophthalmology. These areas may include, for example, protection of hair follicles and rectum from radiation damage during radiation therapy for cancer and amelioration of irritation and inflammation during laser surgery of the eye, including trabeculectomy treatment for glaucoma and keratectomy for corneal reshaping.

While the present invention has been particularly shown and described with reference to the presently preferred embodiments thereof, it is understood that the invention is not limited to the embodiments specifically disclosed herein. Numerous changes and modifications may be made to the preferred embodiment of the invention, and such changes and modifications may be made without departing from the spirit of the invention. It is therefore intended that the appended claims cover all such equivalent variations as they fall within the true spirit and scope of the invention.

EXAMPLES

The present invention is illustrated in certain embodiments by reference to the following examples. The examples are for purposes of illustration only and are not intended to be limiting in any way.

Example 1

Determination of Ester Compound Stability in Aqueous Solution

Method:
A 0.1-0.5% solution of the ester compound was prepared in buffer (pH 4.5-5.0) containing DTPA or EDTA. The solution was filled into amber glass vials, which were sealed and placed in a controlled temperature container maintained at 40° C. Sample vials were removed periodically and stored at 0-5° C. until analyzed by HPLC, GC, or GC/MS analytical methods, and found to be stable after 3 months under these conditions.

To be useful as an anti-cataract drug the agent must penetrate into the lens. This may be included in the method for selecting an anti-cataract compound. A description of method for tempol-H follows:

Example 2

Drug Penetration of Organ Cultured Rat Lenses

In contrast to drugs tested previously as anti-cataract agents, tempol-H and tempol have a remarkable ability to penetrate lens tissue from the surrounding fluid. The experiments described in this section determined the time course, active compound concentrations and compound distribution in the lens, after incubation with rat lenses under the organ culture conditions.

Method:

Rat lenses were cultured as follows: Rat lenses were obtained from Sprague-Dawley rats. The lenses were incubated in 24-well cluster dishes in modified TC-199 medium and were placed in a 37° C. incubator with a 95% air/5% $CO_2$ atmosphere. The lenses were incubated in 2 ml of culture medium, which was adjusted to 300 milliosmoles (mOsm). Lenses were incubated, for 1 to 24 hours, in the culture medium with 4.0 mM tempol-H, or with 4.0 mM of the oxidized form, tempol. At the appropriate time, the lenses were removed from the medium, blotted dry, homogenized and were analyzed for active compound by electron spin resonance method (ESR). In one experiment, lenses were incubated for 4 hours and dissected into epithelial, cortical and nuclear sections before analysis.

Results:

Concentrations (mM, in lens water) of tempol-H reached 0.4 mM, 0.8 mM and 1.0 mM, respectively, after 1, 2 and 4 hours incubation of active compound. Levels of tempol-H found, after incubation of lenses with the oxidized form tempol, reach 0.6 mM, 1.5 mM and 2.8 mM respectively. In the latter case, only a trace (5% or less) of the oxidized form tempol, was found in the lens; it was almost completely converted to the reduced form tempol-H.

Distribution of tempol-H between the lens epithelium, cortex and nucleus was fairly even, after a 4-hour incubation period with tempol-H. Levels of tempol-H reached 1.5 mM, 0.8 mM and 1.0 mM, respectively, in the epithelium, cortex and nucleus. Levels of tempol-H/tempol in lenses incubated with the oxidized form, tempol, were 1.2 mM, 2.9 mM and 2.0 mM, respectively. In the latter case, all compounds in the nucleus were in the reduced form with only about 5% in the epithelium in the oxidized form.

Conclusion:

Both the reduced and oxidized forms of the active agent readily penetrated into the cultured rat lens from the bath medium and distributed to the epithelium, cortex and nucleus. Incubation of lenses with the oxidized form tempol, results in high concentrations of reduced compound tempol-H throughout the lens.

Example 3

1-oxyl-4-(3'-ethoxy-2',2'-dimethyl)propanecarbonyloxy-2,2,6,6-tetramethylpiperidine

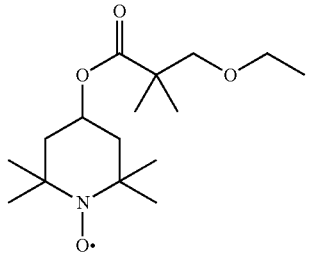

1,1'-carbonyldiimidazole was added in small portion (1.27 g, 7.84 mmol) to a stirred solution of 3-ethoxy-2,2-dimethyl-propionic acid (750 mg, 7.13 mmol; prepared according to the procedure described in J. Org. Chem., 38, 2349,1975, the content of which was incorporated herein by reference) in dry DMF (10 mL). A vigorous gas evolution was observed. This solution was heated at 100° C. for 1 h. To this mixture was then added tempol (900 mg, 5.23 mmol) and 1,8-diazabicyclo[5,4,0]undec-7-ene (DBU) (800 mg, 5.26 mmol) and continue heating for 12 h. The reaction mixture was concentrated under reduced pressure. The residue was dissolved in ethyl acetate (100 mL) and was washed successively with 1N HCl, saturated $NaHCO_3$ and brine, was dried over anhydrous sodium sulfate and was concentrated in vacuo to give red colored solid (1.48 g). This was purified by column chromatography on silica gel using cyclohexane: ethyl acetate (8:1) as eluent to give a red colored crystalline solid (1.22 g, 70.0%).

IR (KBr, cm-1): 1360 (N—O●), 1725 (ester)

Example 4

1-hydroxy-4-(3'-ethoxy-2',2'-dimethyl)propanecarbonyloxy-2,2,6,6-tetramethylpiperidine hydrochloride

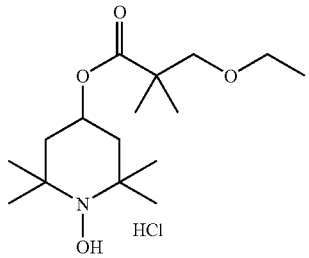 [SMILES: CCOCC(C)(C)C(=O)OC1CC(C)(C)N(O)C(C)(C)C1 ; Cl]

The nitroxide of Example 2 (1.02 mg, 3.34 mmol) was added to a solution of saturated hydrogen chloride in ethanol (20 mL). The red color disappears quickly and the resulting yellow colored solution was boiled to give a clear colorless solution. The solution was concentrated in vacuo, was dissolved in 100 mL ethyl acetate and was washed with saturated $NaHCO_3$ to obtain the hydroxylamine free-base. The ethyl acetate layer was separated and concentrated to give a red colored oil which was mostly nitroxide, by TLC. This oil was purified by column chromatography on silica gel using cyclohexane:ethyl acetate (4:1) as eluent to give a red colored crystalline solid (700 mg). The solid was dissolved in a solution of saturated hydrogen chloride in ethanol (20 mL), was concentrated in vacuo, and was recrystallized from ethyl acetate:diisopropylether (2:1, 50 mL) to give white crystalline solid (320 mg). m.p. 140-142° C. (dec.).

$^1$H-NMR (270 MHz, $D_2O$) ppm: 1.48 (6H, s); 1.57 (3H, t); 1.63 (12H, s); 1.82 (2H, s); 2.02 (2H, t); 2.40 (2H, d), 3.88 (2H, q); 5.44 (1H, m)

IR (KBr, cm-1): 3487 (OH), 1726 (ester)

Mass Spec. (EI, m/z) 301 (M+)

Example 5a 1-oxyl-4-cyclopropanecarbonyloxy-2,2,6,6-tetramethylpiperidine

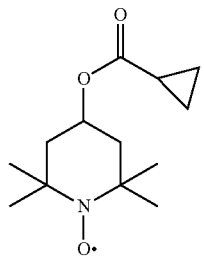

A suspension of sodium hydride (60% in oil, 1.0 g, 25 mmol) in dry THF (50 mL) was stirred at room temperature for 5 min and to this mixture was added tempol (4.0 g, 23 mmol). The mixture was stirred for 1 h, cyclopropanecarbonyl chloride (2.4 g, 23 mmol) was added dropwise over 5 min and then it was refluxed for 1 h. The reaction mixture was concentrated under reduced pressure. The residue was taken up in pentane (100 mL) and the supernatant was separated and concentrated under reduced pressure to give red solid. This solid was purified by column chromatography on silica gel using cyclohexane:ethyl acetate (3:1) as eluent to give a red colored crystalline solid (1.4 g, 5.8 mmol, 25.3%).

IR (KBr, cm-1): 1361 (N—O•), 1720 (ester)

Example 5b

Alternative Method 1-oxyl-4-cyclopropanecarbonyloxy-2,2,6,6-tetramethylpiperidine

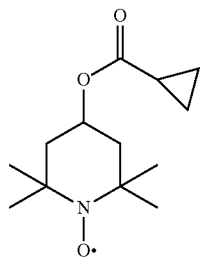

1,1'-Carbonyldiimidazole (1.78 g, 11 mmol) was added in small portions to a stirred solution of cyclopropanecarboxylic acid (860 mg, 10 mmol) in dry DMF (10 mL). A vigorous gas evolution was observed. This solution was heated at 40° C. for 1 h. To this mixture was then added tempol (1.72 g, 10 mmol) and 1,8-diazabicyclo[5,4,0]undec-7-ene(DBU) (1.52 g, 10 mmol) and it was heated at 40° C. for another 12 h. The reaction mixture was concentrated under reduced pressure. The residue was dissolved in ethyl acetate (100 mL) and was washed successively with 1N HCl, saturated NaHCO$_3$ and brine. The ethyl acetate layer was separated, dried over anhydrous sodium sulfate and concentrated in vacuo to give red colored solid. This solid was purified by column chromatography on silica gel using cyclohexane:ethyl acetate (8:1) as eluent to give a red colored crystalline solid (720 mg, 30.0%).

IR (KBr, cm$^{-1}$): 1360 (N—O•), 1720 (ester)

Example 5c

Alternative Method 1-oxyl-4-cyclopropanecarbonyloxy-2,2,6,6-tetramethylpiperidine DCC/DMAP Esterification Method

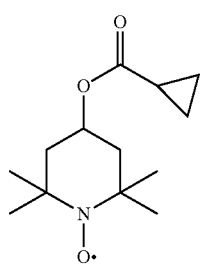

To a stirred solution of Tempol (1.72 g, 0.01 mmole), cyclopropanecarboxylic acid (0.946 g, 0.011 mmole), and DMAP (0.12, 0.001 mmole) in dichloromethane (25 ml) was added DCC (2.27 g, 0.11 mmole) and the mixture was stirred overnight at room temperature. The mixture was filtered over celite and the solution was evaporated under reduced pressure. The product was isolated by silica gel column chromatography using first hexane and then 10% ethyl acetate in hexane. Yield: 2.26 g (94.1). IR and NMR were consistent with the assigned structure.

Example 6

1-hydroxy-4-cyclopropanecarbonyloxy-2,2,6,6-tetramethylpiperidine hydrochloride

Compound 1

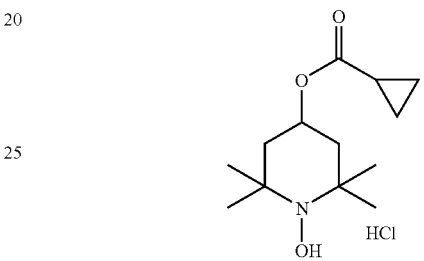

The nitroxide of Example 5a (2.2 g, 9.15 mmol) was added to a solution of saturated hydrogen chloride in ethanol (20 mL). The red color disappeared quickly and the resulting yellow colored solution was boiled to give clear colorless solution. The solution was concentrated in vacuo, dissolved in 100 mL ethyl acetate and was washed with saturated NaHCO$_3$ to obtain the hydroxylamine free-base. The ethyl acetate layer was separated, acidified with ethereal HCl, and concentrated to give white solid, which was recrystallized from ethanol (10 mL) as a white crystalline solid 1.15 g (4.13 mmol, 45.1%). m.p. 224-228° C. (dec.).

$^1$H-NMR (270 MHz, D$_2$O) ppm: 0.97 (4H, d); 1.43 (1H, m); 1.44 (6H, s), 1.46 (6H, s); 1.90 (2H, t); 2.28 (2H, t); 5.2 (1H, m)

IR (KBr, cm-1): 3478 (OH), 1720 (ester)
Mass Spec. (EI, m/z) 240 (M+)

Example 7

1-hydroxy-4-cyclopropanecarbonyloxy-2,2,6,6-tetramethylpiperidine hydrochloride

Alternate Method

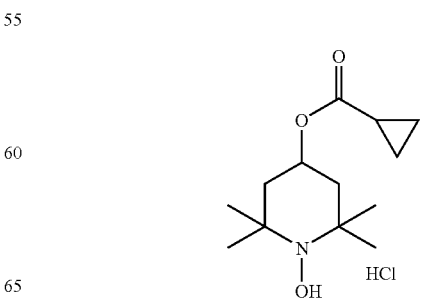

The nitroxide of Example 5a (700 mg, 2.91 mmol) was added to a solution of saturated hydrogen chloride in ethanol (20 mL). The red color disappeared quickly and the resulting yellow colored solution was boiled to give a clear colorless solution. The solution was concentrated in vacuo, dissolved in 100 mL ethyl acetate and concentrated to half volume to give a white crystalline solid, 627 mg (2.25 mmol, 77.5%.). m.p. 224-227° C. (dec.).

$^1$H-NMR (270 MHz, D2O) ppm: 0.97 (4H, d); 1.43 (1H, m); 1.44 (6H, s), 1.46 (6H, s); 1.90 (2H, t); 2.28 (2H, t); 5.2 (1H, m)

IR (KBr, cm-1): 3476 (OH), 1720 (ester)

Mass Spec. (EI, m/z) 240 (M+)

Example 8

1-oxyl-4-(3'-benzyloxy-2',2'-dimethyl)propanecarbonyloxy-2,2,6,6-tetramethylpiperidine

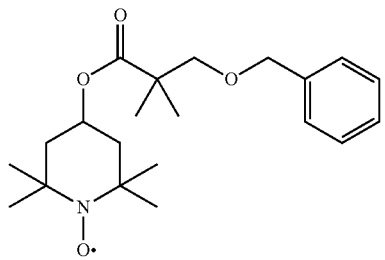

To a stirred solution of 3-benzyloxy-2,2-dimethylpropionic acid (1.04 g, 5 mmol), (prepared by a method similar to that described in J. Org. Chem., 38, 2349,1975), in dry DMF (5 mL), was added 1,1'-carbonyldiimidazole in small portions. A vigorous gas evolution was observed. This solution was heated at 50° C. for 30 min. To this mixture was then added tempol (900 mg, 5.23 mmol) and 1,8-diazabicyclo[5,4,0]undec-7-ene(DBU) (800 mg, 5.26 mmol). The mixture was heated at 50° C. for 3 days (monitored by TLC) and then it was concentrated under reduced pressure. The residue was dissolved in ethyl acetate (100 mL), washed successively with 1N HCl, saturated NaHCO$_3$ and brine, and dried over anhydrous sodium sulfate. The dried solution was concentrated in vacuo to give red colored solid (1.48 g). This solid was purified by column chromatography on silica gel using cyclohexane:ethyl acetate (3:1) as eluent to give a red colored crystalline solid (1.02 g, 2.8 mmol, 56.2%).

IR (KBr, cm-1): 1359 (N—O●), 1732 (ester)

Example 9

1-hydroxy-4-(3'-benzyloxy-2',2'-dimethyl)propanecarbonyloxy-2,2,6,6-tetramethylpiperidine hydrochloride

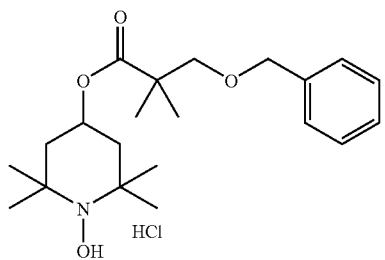 [SMILES: CC(C)(COCc1ccccc1)C(=O)OC1CC(C)(C)N(O)C(C)(C)C1 ; Cl]

The nitroxide of Example 8 (1.02 mg, 3.34 mmol) was added to a solution of saturated hydrogen chloride in ethanol (20 mL). The red color disappears quickly and the resulting yellow colored solution was boiled to give clear colorless solution. The solution was concentrated in vacuo and the residue dissolved in ethyl acetate (20 mL). Hexane (20 mL) was added and product began to oil out; the mixture was then allowed to stand for 12 h. An oily residue was obtained by decantation of the solvent and it was treated with was isopropyl ether and warmed. Upon cooling the mixture, a waxy solid was obtained and recrystallized from ethyl acetate to give white crystalline solid (0.6 g, 1.5 mmol, 45%).

$^1$H-NMR (270 MHz, D$_2$O) ppm: 1.26 (6H, s), 1.51 (6H, s); 1.65 (6H, s); 2.01 (2H, t); 2.44 (2H, d), 5.40 (1H, m); 3.46 (2H, s), 4.55 (2H, S), 7.31 (5H, s)

IR (KBr, cm-1): 3480 (OH), 1712 (ester), 710 (aromatic)

Mass Spec. (EI, m/z) 262 (M+)

Example 10

1-hydroxy-4-(3'-hydroxy-2',2'-dimethyl)propanecarbonyloxy-2,2,6,6-tetramethylpiperidine hydrochloride

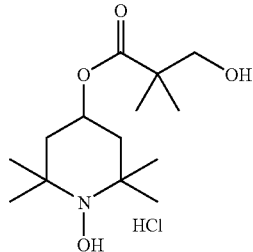 [SMILES: CC(C)(CO)C(=O)OC1CC(C)(C)N(O)C(C)(C)C1 ; Cl]

Pd/C (5%, 100 mg) was added to a solution of 1-oxyl-4-(3'-benzyloxy-2',2'-dimethyl)propanecarbonyloxy-2,2,6,6-tetramethylpiperidine (1.0 g, 3.83 mmol) in ethanol, and the mixture was hydrogenated in a Paar hydrogenation apparatus at 45 psi for 12 h. The reaction mixture was filtered through celite and concentrated in vacuo to give a clear colorless oil, which was purified by column chromatography on silica gel using cyclohexane:ethyl acetate (3:1) as eluent to give a colorless oil. The oil was dissolved in a solution of saturated hydrogen chloride in ethanol (20 mL) and concentrated in vacuo. Product crystallized upon standing, and was recrystallized from ethanol (123 mg, 0.4 mmol, 10.4%). m.p. 210-215° C. (dec.).

$^1$H-NMR of the free base (270 MHz, CDCl$_3$) ppm: 1.14 (6H, s), 1.44 (6H, s); 1.57 (6H, s); 1.70 (2H, m); 2.8 (1H, s, br), 3.65 (2H, s) 5.16 (1H, m)

IR (KBr, cm-1): 3480 (OH), 1712 (ester), 710 (aromatic)

Mass Spec. (EI, m/z) 262 (M+)

Example 11

1-oxyl-4-(1-methyl-cyclopropane)carbonyloxy-2,2,6,6-tetramethylpiperidine

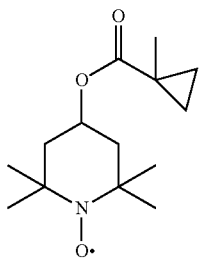

A suspension of sodium hydride (60% in oil 2.2 g), in dry THF (80 mL) was stirred at room temperature for 5 min and then tempol (3.0 g, 17.44 mmol) was added. The mixture was stirred for 30 min, 1-methyl-cyclopropanecarbonyl chloride (2.2 g, 18.71 mmol) was added drop wise over 5 min and then it was refluxed for 12 h. The reaction mixture was concentrated under reduced pressure and the residue crystallized immediately. The product was purified by column chromatography on silica gel using cyclohexane:ethyl acetate (3:1) as eluent to give a red colored crystalline solid (2.0 g, 7.86 mmol, 45.1%).

IR (KBr, cm-1): 1314 (N—O●), 1722 (ester)

Example 12

1-hydroxy-4-(1-methyl-cyclopropane)carbonyloxy-2,2,6,6-tetramethylpiperidine hydrochloride

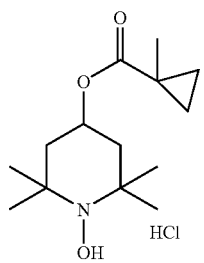 [SMILES: CC1(C(=O)OC2CC(C)(C)N(O)C(C)(C)C2)CC1 ; Cl]

The nitroxide of Example 11 (700 mg, 2.91 mmol) was added to a solution of saturated hydrogen chloride in ethanol (10 mL). The red color disappears quickly and the resulting yellow colored solution was boiled to give a clear colorless solution. The solution was concentrated in vacuo to give white crystalline solid, which was filtered, washed with ethyl acetate and dried in vacuo (0.700 mg, 2.4 mmol, 82.7%) m.p. 215° C.-220° C. (dec.).

$^1$H-NMR (270 MHz, D$_2$O) ppm: 0.80 (2H, d); 1.19 (2H, m); 1.21 (2H, s); 1.44 (15H, s); 2.03 (4H, m); 5.10 (1H, m)

Mass Spec. (EI, m/z) 254 (M+)

Example 13

1-oxyl-4-(2-furan)carbonyloxy-2,2,6,6-tetramethylpiperidine

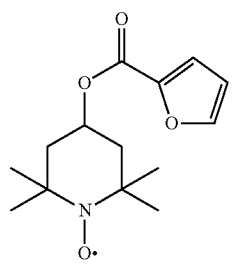

A stirred mixture of sodium methoxide (25% sodium methoxide in methanol, 200 mg) in benzene (100 mL) was heated to reflux and the benzene was gradually distilled off to half volume to obtain a fine suspension of solid sodium methoxide. To this mixture was added tempol (1.76 g, 10 mmol), methyl 2-furoate (1.26 g, 10 mmole) and benzene (50 mL). Distillation of benzene was continued for 8 h to remove formed methanol. The volume of benzene in the flask was maintained by adding more benzene. The benzene layer was washed with 1 N HCl, then with water, dried over anhydrous sodium sulfate and evaporated to dryness to give a red solid (1.72 g), which was recrystallized from hexane to give 1.45 g of product. It was further purified by column chromatography on silica gel using cyclohexane:ethyl acetate (3:1) as eluent to give a red colored crystalline solid (1.02 g, 3.82 mmol, 32.8%).

IR (KBr, cm-1): 1364 (N—O●), 1716 (ester), 706 (aromatic)

Example 14

1-hydroxy-4-(2'-furan)carbonyloxy-2,2,6,6-tetramethylpiperidine hydrochloride

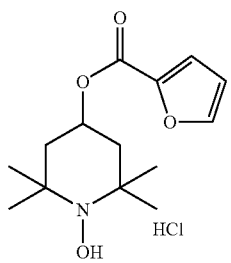 [SMILES: CC1(C)CC(OC(=O)c2ccco2)CC(C)(C)N1O ; Cl]

The nitroxide of Example 13 (300 mg, 1.13 mmol) was added to a solution of saturated hydrogen chloride in ethanol (10 mL). The red color disappeared quickly and the resulting yellow colored solution was boiled to give clear colorless solution. The solution was kept at room temperature for 1 h and a white crystalline solid separated. It was filtered, washed with ethyl acetate and dried in vacuo to afford the hydroxylamine (220 mg, 0.72 mmol, 64.5%, m.p. 209.4° C.-210.4° C.).

$^1$H-NMR (270 MHz, D$_2$O) ppm: 1.49 (6H, s); 1.62 (6H, s); 2.03 (2H, t); 2.42 (2H, d), 5.49 (1H, m); 6.63 (1H, q); 6.64 (1H, d), 7.34 (1H, d), 7.74 (1H, s)

Mass Spec. (EI, m/z) 266 (M+)

Example 15

1-oxyl-4-(3'-tetrahydrofuran)carbonyloxy-2,2,6,6-tetramethylpiperidine

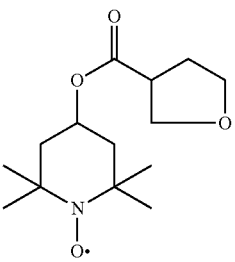

To a stirred solution of 3-tetrahydrofuancarboxylic acid (1.5 g, 13 mmol) in dry DMF (20 mL) was added 1,1'-carbonyldiimadazole (2.3 g, 14.18 mmol) in small portions. A vigorous gas evolution was observed. This solution was heated at 70° C. for 1 h. To this mixture was then added tempol (2.23 g, 12.97 mmol) and 1,8-diazabicyclo[5,4,0]undec-7-ene(DBU) (2.0 g, 13.14 mmol) and heating was continued for 12 h. The reaction mixture was poured into 250 mL water and extracted with ether (2×100 mL). The ethereal layers were combined and washed successively with 1N HCl, saturated NaHCO$_3$ and brine, dried over anhydrous sodium sulfate and concentrated in vacuo to give red colored solid (2.05 g), that recrystallized from ethyl acetate:Hexane (1:2) to obtain pure red crystalline solid nitroxide (1.45 g, 5.36 mmol, 37.8%).

IR (KBr, cm-1): 1360 (N—O●), 1725 (ester)

Example 16

1-hydroxy-4-(3'-tetrahydrofuran)carbonyloxy-2,2,6,6-tetramethylpiperidine hydrochloride

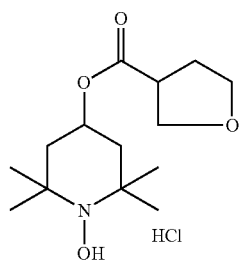 [SMILES: CC1(C)CC(OC(=O)C2CCOC2)CC(C)(C)N1O ; Cl]

The nitroxide of Example 15 (300 mg, 1.11 mmol) was added to a solution of saturated hydrogen chloride in ethanol (10 mL). The red color disappeared quickly and the resulting yellow colored solution was boiled to give a clear colorless solution. The solution was kept at room temperature for 1 h and a white crystalline solid separated. The solid was filtered, washed with ethanol and dried in vacuo to afford product (146 mg, 0.48 mmol, 42.86%, m.p. 221.0° C.-223.2° C.).

$^1$H-NMR (270 MHz, DMSO-d$_6$) ppm: 0.84 (2H, m); 0.90 (2H, m); 1.35 (6H, s); 1.46 (6H, s); 1.65 (1H, m); 2.13 (2H, t); 2.44 (2H, d), 5.14 (1H, m)

Example 17

Absorption of Representative Compounds Across the Corneas of Animals

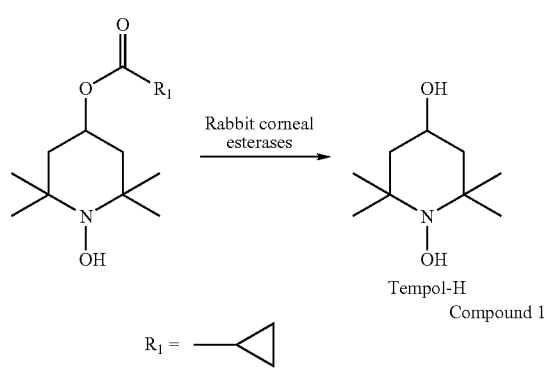

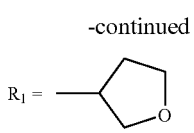
Compound 2

Compound 3

Groups of six New Zealand White rabbits were used in the study to evaluate the absorption of tempol-H and compound 1. The test compounds were prepared in sterile saline solutions at a concentration of 3.5% weight by volume. The animals were held in restraining boxes during instillation of eye drops, 50 µL in each eye, using a micropipette. After dosing, the eye was gently held closed for 60 seconds. The rabbits were dosed twice daily for 4 consecutive days. On the fifth day, rabbits were dosed once and then euthanized at 30 minutes post dose (2 rabbits), 60 minutes post-dose (2 rabbits) and at 120 minutes post-dose (2 rabbits). Immediately after euthanization, aqueous humor was collected from each rabbit. The aqueous concentration of tempol-H in each sample was measured using the electron spin resonance (ESR) method.

Aqueous humor levels of tempol-H after dosing with tempol-H, were below detectable limits of the assay at all time points (see FIG. 1). Aqueous humor concentrations of tempol-H after dosing with compound 1 were maximal at 30 minutes post-dose but were still present at 2 hours post-dose. (see FIG. 1 and Table 1).

TABLE I

Aqueous Humor Concentrations: Absorption Studies in Rabbits
Dose: 50 µL of 3.5% solution, single dose (N = 4 eyes/timepoint)
Concentration of Tempol-H µM

|  | 30 minutes | 60 minutes | 120 minutes |
| --- | --- | --- | --- |
| Compound 1 | 51.0 | 20.0 | 1.5 |
|  | 30.0 | 30.0 | 1.2 |
|  | 18.0 | 6.0 | 7.0 |
|  | 30.0 | 3.0 | 8.0 |
| Mean | 32.3 | 14.8 | 4.4 |
| µg/ml | (5.5) | (2.5) | (0.75) |

Example 18

Identification of Metabolites of Compound 1 in Rabbit Eye

Aqueous humor samples, from the in vivo rabbit study described in Example 16 were identified by GC/MS for the presence of compound 1 and its metabolites, tempol-H and carboxylic acid (R$_1$COOH), formed by hydrolysis of compound 1 by ocular esterases. Both the metabolites were observed but not Compound 1. This confirmed that Compound 1 was completely converted to its metabolites.

A sample of aqueous humor was freeze dried in a 10 mL amber colored glass vial containing a tiny magnetic bar. To this was added 1 mL of methylene chloride and the solution was stirred for two minutes and allowed to stand for five minutes. A 3 µL aliquot of the methylene chloride layer was injected into the GC column. The cyclopropanecarboxylic acid was detected by a mass spectrometer detector at 13.02 (retention time) with m/z=85 (GC model 5989B and MS model 5890 series II (both made by HP)). Agilent DB-5 column 25 m length, 0.2 mm diameter was used. Carrier gas He at 22 cm/sec. Inlet temperature was 250° C., detector 280° C. For every injection, the temperature was held at 35° C. for 5 minutes, then was increased to 240° C. at 10° C./min, and was held at 240° C. for 3 minutes. Splitless injection was used.

Example 19

Tolerance of Compound 1 In Vivo in Rabbit Eyes

Eyedrops containing 3.5% compound 1 were administered six times, at 1-hour intervals, to each eye of two conscious rabbits. The drug was well tolerated and no adverse findings were noted in this preliminary study.

Example 20

Ocular Bioavailability in Rabbit

The ocular bioavailability of compounds 2 and 3 was evaluated in New Zealand White rabbits. Each compound was dissolved in 10 mM phosphate buffer, pH 7.0 to a concentration of 125 mM. This concentration was equal to ~3.5% for compounds 2 and 3. Fifty μl was instilled onto the cornea of both eyes of each rabbit 6 times at 1-hour intervals. Two rabbits were used for each compound. One rabbit treated with each compound was euthanized 30 minutes after the last dose and the second was euthanized 90 minutes after the final dose.

After death, the eyes of each rabbit were immediately enucleated and a blood sample was collected from the orbit. Aqueous humor was collected from each eye with a syringe and then the lens was dissected from the eye. The capsule/epithelium was carefully separated from the fiber mass and both parts were frozen on dry ice, the capsule/epithelium in 100 l of 5 mM DTPA (diethylenetriaminepentaacetic acid) solution and the fiber mass in a sealed vial without added liquid. Likewise, the aqueous and blood samples were quick frozen. The rest of each eye including the cornea, retina, sclera and vitreous were frozen for possible future dissection and analysis. All samples were transported to the lab on dry ice and were stored at −75° C. until processed.

The aqueous concentration of tempol-H in each sample was measured using the electron spin resonance (ESR) method. Analysis of the aqueous humor reveals that both compounds penetrated the cornea and entered the aqueous chamber. The highest concentrations for both compounds was present in the 30-minute sample with the 90-minute samples being significantly reduced in concentration. Small amounts (2-3 M of each compound) were also detected in the blood.

Example 21

Aqueous Humor Concentrations of Compounds 2 and 3; in Rabbits

TABLE II

Dose of Compound 2 and 3: 50 μL of 125 mM solution, at hourly intervals × 6 (N = 2 eyes/timepoint)
Concentration of Tempol-H μM

|  | 30 minutes | 90 minutes | Blood |
|---|---|---|---|
| Compound 3 | 31.4 | 11.6 | 2.3 |
|  | 22.2 | 9.0 | 2.5 |

TABLE II-continued

Dose of Compound 2 and 3: 50 μL of 125 mM solution, at hourly intervals × 6 (N = 2 eyes/timepoint)
Concentration of Tempol-H μM

|  | 30 minutes | 90 minutes | Blood |
|---|---|---|---|
| Mean | 26.8 | 10.8 | 2.4 |
| μg/ml | (4.6) | (1.9) | (0.4) |
| Compound 2 | 52.4 | 6.0 | 3.6 |
|  | 35.2 | 5.7 | 0.6 |
| Mean | 43.8 | 5.9 | 2.1 |
| μg/ml | (7.5) | (1.0) | (0.4) |

Example 22

Aqueous Solubility Data

TABLE III

Solubility of Compound of Example 6 determined at room temperature in various systems.

| Conditions | Solubility mg/ml | Solubility % w/v |
|---|---|---|
| Water | 74.9 | 7.5 |
| 0.9% Sodium chloride | 40.5 | 4.1 |
| 0.01M Acetate buffer at pH 4.8 | 68.6 | 6.9 |
| 0.01M Citrate buffer at pH 4.8 | 71.1 | 7.1 |
| Water + 1% w/v glycerin | 62.2 | 6.2 |
| Water + 1% w/v propylene glycol | 63.8 | 6.4 |

Similarly, the solubility compounds of Examples 10 and 16 in water were determined to be >3.5% w/v (>35 mg/ml) in water whereas the compound of Example 12 is soluble at approximately 0.1% w/v in water.

TABLE IV

Partition Coefficient of Ester Compounds

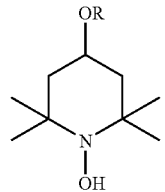

| Examples | R | Calculated PC |
|---|---|---|
| 23 | H | 0.8 |
| 24 | -) | 7.2 |
| 25 | -) | 16.2 |
| 26 | -) | 50.1 |

TABLE IV-continued

Partition Coefficient of Ester Compounds

Structure: 4-OR-2,2,6,6-tetramethylpiperidine-1-ol (N–OH)

| Examples | R | Calculated PC |
|---|---|---|
| 27 | –C(=O)–C(CH₃)(cyclopropyl) | 53.7 |
| 28 | –C(=O)–C(CH₃)₃ | 125.9 |
| 29 | –C(=O)–(3-furyl) | 91.2 |
| 30 | –C(=O)–(3-tetrahydrofuryl) | 6.3 |
| 31 | –CH₂–C(CH₃)₂–CH₂–O–CH₂CH₃ | 114.8 |
| 32 | –CH₂–C(CH₃)₂–CH₂–O–CH₃ | 34.7 |
| 33 | –CH₂–C(CH₃)₂–CH₂–S–CH₃ | 199.5 |
| 34 | –CH₂–C(CH₃)₂–CH₂–S(=O)–CH₃ | 4.3 |
| 35 | –CH₂–C(CH₃)₂–CH₂–OH | 8.1 |
| 36 | –CH₂–C(CH₃)₂–CH₂–O–C(=O)–cyclopropyl | 144.5 |
| 37 | –CH₂–C(CH₃)₂–CH₂–NH₂ | 10 |
| 38 | –CH₂–C(CH₃)₂–CH₂–N(CH₃)₂ | 51.3 |
| 39 | –CH₂–C(CH₃)₂–CH₂–N(CH₂CH₃)₂ | 575.4 |
| 40 | –CH₂–C(CH₃)₂–CH₂–(morpholin-4-yl) | 34.7 |
| 41 | –CH₂–C(CH₃)₂–CH₂–(piperidin-1-yl) | 69.4 |
| 42 | –CH₂–C(CH₃)₂–CH₂–(4-oxopiperidin-1-yl) | 67.6 |
| 43 | –CH₂–C(CH₃)₂–CH₂–(1-methylpyrrol-2-yl) | 39.8 |

TABLE V

Melting Points of Ester Compounds

Structure: 4-(O–C(=O)–R₂)-2,2,6,6-tetramethylpiperidine with N–R₁

| Examples | R1 | R2 | M.P. (° C.) |
|---|---|---|---|
| 44 | O | cyclopropyl | 97.2–98.2 |
| 44 | OH (as HCl salt) | cyclopropyl | 224–228° C. (dec.). |
| 45 | OH (as HCl salt) | cyclopropyl | 224–227° C. (dec.). |
| 46 | O | 2-furyl | 103.9–105.2 |

TABLE V-continued

Melting Points of Ester Compounds

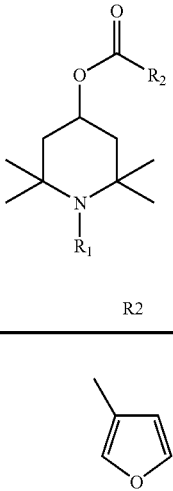

| Examples | R1 | R2 | M.P. (° C.) |
|---|---|---|---|
| 47 | OH (as HCl salt) | 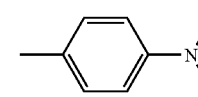 | 209.4-210.1 |
| 48 | O | 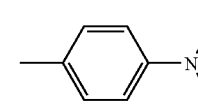 | 150-152.3 |
| 49 | OH (as HCl salt) | 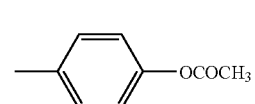 | 250.6-253.2 |
| 50 | O | 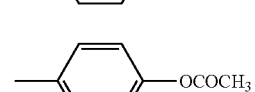 | 64.8-66.1 |
| 51 | OH (as HCl salt) | 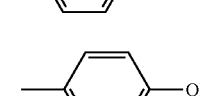 | 229.0-230.9 |
| 52 | O | 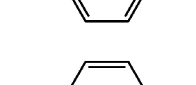 | 107-109.3 |
| 53 | OH (as HCl salt) | 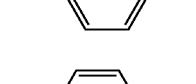 | 220.0-223.0 |
| 54 | O | 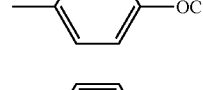 | 111.1-112.3 |
| 55 | OH (as HCl salt) | 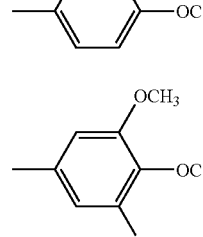 | 228.0-231.2 |
| 56 | O | 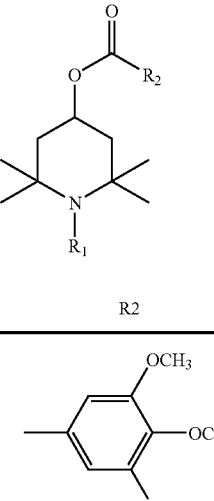 | 121.2-122.9 |
| 57 | OH (as HCl salt) | 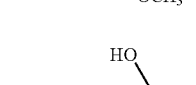 | 241.8-244.6 |
| 58 | O | 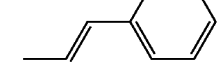 | 145.2-146.4 |
| 59 | OH (as HCl salt) | 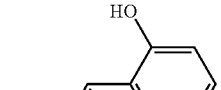 | 237.8-269.1 |
| 60 | O | 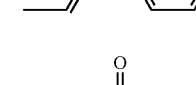 | 132-133.0 |
| 61 | OH (as HCl salt) | 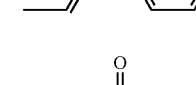 | 267.9-270 |
| 62 | O | 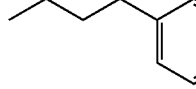 | 68.3-69.9 |
| 63 | OH (as HCl salt) | 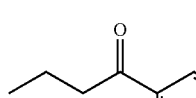 | 264.8-266.3 |

Spectral Data for the Ester Compounds $^1$H-NMR (270 MHz, DMSO-$d_6$) ppm: spectral data that was common to all 4-substituted-1-hydroxy-2,2,6,6-tetramethylpiperidine hydrochloride portion 1.35 (6H, s); 1.46 (6H, s); 2.13 (2H, t); 2.44 (2H, d); 5.14 (1H, m)

| Examples | IR CKBr) cm-1 Carbonyl(s) | $^1$H-NMR (270 MHz, DMSO-$d_6$) ppm: for the ester moiety |
|---|---|---|
| 57 | 1716 | 3.75 (S, 9H); 6.95 (s, 2H) |
| 61 | 1738 1687 | 2.79 (t, 2H); 3.31 (t, 2H); 7.45 (m, 2H); 7.55 (m, 1H); 7.93 (d, 2H) |
| 53 | 1682 | 6.87 (d, 2H); 7.83 (d, 2H), 10.3 (br, s, 1H) |
| 51 | 1718 1755 | 3.9 (s, 3H), 7.18 (d, 2H), 8.07 (d, 2H) |
| 59 | 1723 | 6.54, 7.85 (dd, J = 16.0 Hz); 6.84 (m, 1H); 7.24 (m, 1H); 7.54 (d, 1H); 7.86 (d, 1H); 10/2 (br, s, 1H) |
| 61 | 1718 | 1.96 (m, 2H); 2.30 (m, 4H); 2.78 (m, 2H) |
| 49 | 1688 | 2.88 (S, 6H); 6.65 (d, 2H); 7.73 (d, 2H) |
| 53 | 1682 | 3.70 (s, 3H); 7.20 (d, 2H); 7.72 (d, 2H) |

The following Tables VI to XII describe methods used in the synthesis of additional examples of the ester compounds of the invention. The appropriate carboxylic acid listed in the Tables is converted to the ester nitroxide by the DCC/DMAP esterification method of Example 5c. The ester nitroxide is converted to the corresponding 1-hydroxypiperidine by the methods described in Examples 6 and 7.

3-acyloxy-2.2-dimethylpropionic acids were prepared by the method described in U.S. Pat. No. 4,851,436, the content of which is incorporated herein by reference, for the synthesis of 3-acetoxy-2,2-dimethylpropionic acid.

TABLE VI

Substitute cyclopropanecarboxylic acid with following compounds in DCC/DMAP esterification method:

| Examples | Starting material (structure) | Chemical name |
|---|---|---|
|  | [structure] | 3-Acetoxy-2,2-dimethylpropionic acid |
|  | [structure] | 3-Pivaloloxy-2,2-dimethylpropionic acid |
|  | [structure] | 3-Cyclopropane-carbonyloxy-2,2-dimethylpropionic acid |
|  | [structure] | 3-(1-Methyl-cyclopropane-carbonyloxy)-2,2-dimethylpropionic acid |
|  | [structure] | 3-(2-Methyl-cyclopropane-carbonyloxy)-2,2-dimethylpropionic acid |
|  | [structure] | 3-(2,2-Dimethyl-cyclopropane-carbonyloxy)-2,2-dimethylpropionic acid |

TABLE VI-continued

Substitute cyclopropanecarboxylic acid with following compounds in DCC/DMAP esterification method:

| Examples | Starting material (structure) | Chemical name |
|---|---|---|
|  | [structure] | 3-(3-Tetrahydrofuran-carbonyloxy)-2,2-dimethylpropionic acid |
| 64 | [structure] | 3-(1-Methyl-3-tetrahydro-furancarbonyloxy)-2,2-dimethyl-propionic acid |

TABLE VII 3-alkoxy-2.2-dimethylpropionic acids and 3-alkoxyalkyl-2.2-dimethylpropionic acids were prepared by the method described in J. Org. Chem. 38, 2349 (1975). Substitute cyclopropane-carboxylic acid with following compounds in the DCC/DMAP esterification method (Example 5c):

| Starting material (structure) | Chemical name |
|---|---|
| [structure] | 3-Methoxy-2,2-dimethylpropionic acid |
| [structure] | 3-propoxy-2.2-dimethylpropionic acid |
| [structure] | 3-isopropoxy-2.2-dimethylpropionic acid |
| [structure] | 3-Cyclopropylmethoxy-2,2-dimethylpropionic acid |
| [structure] | 3-(2-Methoxy-ethoxy)-2,2-dimethylpropionic acid |
| [structure] | 3-Ethoxymethoxy-2,2-dimethylpropionic acid |

TABLE VIII

3-N-substituted-2,2-dimethylpropionic acids are prepared by the method described in U.S. Pat. No. 5,475,013 to Talley et al., the content of which is incorporated herein by reference. Substitute cyclopropanecarboxylic acid with the following compounds in the DCC/DMAP esterification method (Example 5c):

| Starting material (structure) | Chemical name |
|---|---|
| [structure] | 3-Amino-2,2-dimethylpropionic acid |
| [structure] | 3-Dimethylamino-2,2-dimethylpropionic acid |
| [structure] | 2,2-Dimethyl-3-piperidin-1-yl-propionic acid |
| [structure] | 2,2-Dimethyl-3-(4-oxo-piperidin-1-yl)-propionic acid |
| [structure] | 2,2-Dimethyl-3-thiomorpholin-4-yl-propionic acid |
| [structure] | 2,2-Dimethyl-3-(4-methyl-piperazin-1-yl)-propionic acid |
| [structure] | 3-Imidazol-1-yl-2,2-dimethyl-propionic acid |

TABLE IX

3-S-substitted-2,2-dimethylpropionic acids are prepared by the method described in U.S. Pat. No. 5,475,013. Substitute cyclopropanecarboxylic acid with following compounds in the DCC/DMAP esterification method (Example 5c):

| Starting material (structure) | Chemical name |
|---|---|
| [structure] | 2,2-Dimethyl-3-methylsulfanyl-propionic acid |
| [structure] | 3-Methanesulfinyl-2,2-dimethyl-propionic acid |
| [structure] | 2,2-Dimethyl-3-phenylsulfanyl-propionic acid |

TABLE IX-continued

3-S-substitted-2,2-dimethylpropionic acids are prepared by the method described in U.S. Pat. No. 5,475,013. Substitute cyclopropanecarboxylic acid with following compounds in the DCC/DMAP esterification method (Example 5c):

| Starting material (structure) | Chemical name |
|---|---|
| [structure] | 3-Benzenesulfonyl-2,2-dimethyl-propionic acid |

TABLE X

3-Substitted-2,2-dimethylpropionic acids are prepared by the method described in U.S. Pat. No. 5,475,013. Substitute cyclopropanecarboxylic acid with following compounds in the DCC/DMAP esterification method (Example 5c):

| Starting material (structure) | Chemical name |
|---|---|
| [structure] | 2,2-Dimethyl-3-phenylpropionic acid |
| [structure] | 2,2-Dimethyl-3-pyridin-4-yl-propionic acid |

TABLE XI

Various NSAID (nonsteroidal anti-inflammatory drugs containing carboxylic acid group) are commercially available. Substitute cyclopropanecarboxylic acid with following compounds in the DCC/DMAP esterification method:

| Starting material (structure) | Chemical name |
|---|---|
| [structure] | Ketorolac or 5-Benzoyl-2,3-dihydro-1H-pyrrolizine-1-carboxylic acid |
| [structure] | Flurbibrofen or 2-(2-Fluoro-biphenyl-4-yl)propionic acid |
| [structure] | Ibuprofen or 2-(4-Isobutyl-phenyl)propionic acid |
| [structure] | Naproxen or 2-(5-Methoxy-naphthalen-2-yl)propionic acid |

TABLE XI-continued

Various NSAID (nonsteroidal anti-inflammatory drugs containing carboxylic acid group) are commercially available. Substitute cyclopropanecarboxylic acid with following compounds in the DCC/DMAP esterification method:

| Starting material (structure) | Chemical name |
|---|---|
| (structure of aspirin) | Aspirin |

TABLE XII

Various carboxylic acids are commercially available. Substitute cyclopropanecarboxylic acid with the following compounds in DCC/DMAP esterification method:

| Starting material (structure) | Chemical name |
|---|---|
| (structure) | Cyclopent-3-enecarboxylic acid |
| (structure) | But-3-enoic acid |
| (structure) | Tetrahydro-furan-2-carboxylic acid |
| (structure) | Tetrahydro-thiophene-2-carboxylic acid |
| (structure) | Tetrahydro-thiophene-3-carboxylic acid |
| (structure) | 2-Oxo-thiazolidine-4-carboxylic acid |
| (structure) | 2-Oxo-oxazolidine-4-carboxylic acid |

TABLE XII-continued

Various carboxylic acids are commercially available. Substitute cyclopropanecarboxylic acid with the following compounds in DCC/DMAP esterification method:

| Starting material (structure) | Chemical name |
|---|---|
| (structure) | 2-Oxo-imidazolidine-4-carboxylic acid |
| (structure) | 2-Oxo-[1,3]dioxolane-4-carboxylic acid |
| (structure) | 1-Methyl-pyrrolidine-3-carboxylic acid |
| (structure) | 1-methyl-pyrrolidine-2-carboxylic acid |
| (structure) | Tetrahydro-pyran-4-carboxylic acid |
| (structure) | Tetrahydro-thiopyran-4-carboxylic acid |
| (structure) | 1-Methyl-piperidine-4-carboxylic acid |
| (structure) | 3-hydroxy-2-methylpropionic acid |
| (structure) | 3-amino-2-methylpropionic acid |
| (structure) | 3-mercapto-2-methylpropionic acid |
| (structure) | 3-methoxy-2-methylpropionate (synthesis: U.S. Pat. No. 4,617,154, the content of which is incorporated herein by reference) |

What is claimed:

1. A composition comprising a pharmaceutically acceptable carrier or diluent and a compound having the formula:

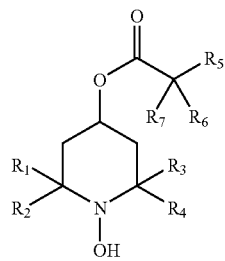

where $R_1$ and $R_2$ are, independently, H or $C_1$ to $C_3$ alkyl;
$R_3$ and $R_4$ are, independently, $C_1$ to $C_3$ alkyl; and
where $R_1$ and $R_2$, taken together, or $R_3$ and $R_4$, taken together, or both may be cycloalkyl;
$R_5$ is H, OH, or $C_1$ to $C_6$ alkyl;
$R_6$ is $C_1$ to $C_6$ alkyl, alkenyl, alkynyl, or substituted alkyl or alkenyl;
$R_7$ is $C_1$ to $C_6$ alkyl, alkenyl, alkynyl, or substituted alkyl or alkenyl
or where $R_6$ and $R_7$, or $R_5$, $R_6$ and $R_7$, taken together, form a heterocycle having from 3 to 7 atoms in the ring.

2. The composition of claim 1 wherein the substituted alkyl or alkenyl has at least one alkoxy, alkylthio, alkylamino, dialkylamino, aryloxy, arylamino, benzyloxy, benzylamino or heterocyclic or YCO—Z where Y is O, N, or S and Z is alkyl, cycloalkyl or heterocyclic or aryl substituent.

3. The composition of claim 1 wherein the heterocycle is a 5, 6, or 7 membered ring with at least one oxygen, nitrogen, or sulfur atom in the ring.

4. The composition of claim 1 wherein $R_6$ and $R_7$, taken together, are furoyl or tetrahydrofuroyl.

5. The composition of claim 1 wherein each of $R_1$ through $R_4$ is $C_1$ to $C_3$ alkyl.

6. The composition of claim 1 wherein each of $R_1$ through $R_4$ is methyl.

7. The composition of claim 1 wherein $R_6$ is $C_1$ to $C_6$ alkyl substituted with at least one $C_1$ to $C_6$ alkoxy or benzyloxy group.

8. The composition of claim 1 wherein each of $R_1$ through $R_4$ is methyl, $R_5$ is H or methyl, $R_6$ is methyl substituted with benzyloxy or $C_1$ to $C_6$ alkoxy, and $R_7$ is methyl.

9. The composition of claim 1 wherein each of $R_1$ through $R_4$ is methyl, $R_5$ is methyl, $R_6$ is ethoxy methyl, and $R_7$ is methyl.

10. The composition of claim 1 wherein each of $R_1$ through $R_4$ is methyl, $R_5$ is methyl, $R_6$ is benzyloxy methyl, and $R_7$ is methyl.

11. The composition of claim 1 wherein each of $R_1$ through $R_4$ is methyl, $R_5$ is methyl, $R_6$ is hydroxymethyl, and $R_7$ is methyl.

12. The composition of claim 1 wherein each of $R_1$ through $R_4$ is methyl and $R_5$, $R_6$, and $R_7$ form a furanyl group.

13. The composition of claim 1 wherein each of $R_1$ through $R_4$ is methyl, $R_5$ is H and $R_6$, and $R_7$ form a tetrahydrofuranyl group.

14. The composition of claim 1 adapted for pharmaceutical use as an eye drop.

15. The composition of claim 1 further comprising a reducing agent.

16. The composition of claim 15 wherein the reducing agent is a sulfhydryl compound.

17. The composition of claim 1 further comprising mercaptopropionyl glycine, N-acetyl cysteine, β-mercaptoethylamine, or glutathione.

* * * * *